US006398772B1

(12) United States Patent
Bond et al.

(10) Patent No.: US 6,398,772 B1
(45) Date of Patent: Jun. 4, 2002

(54) METHOD AND APPARATUS FOR EMERGENCY TREATMENT OF PATIENTS EXPERIENCING A THROMBOTIC VASCULAR OCCLUSION

(75) Inventors: Geoffrey Bond, Jamestown, NY (US); Thomas M. Peterson, Erie, PA (US)

(73) Assignee: Coraje, Inc., San Francisco, CA (US)

( * ) Notice: Subject to any disclaimer, the term of this patent is extended or adjusted under 35 U.S.C. 154(b) by 0 days.

(21) Appl. No.: 09/277,359

(22) Filed: Mar. 26, 1999

(51) Int. Cl.[7] .............................................. A61M 31/00
(52) U.S. Cl. ......................................... 604/507; 604/22
(58) Field of Search .................. 604/19, 20–22, 604/48, 500, 506–508, 511, 93.01, 264, 509–510; 601/2.3; 600/458, 437

(56) References Cited

U.S. PATENT DOCUMENTS 5,380,273 A * 1/1995 Dubrul et al. ................. 604/22
5,498,238 A * 3/1996 Shapland et al. ............. 604/53
5,498,421 A * 3/1996 Grinstaff et al. ............. 424/450
5,695,460 A * 12/1997 Siegal et al. .................. 604/21
5,961,483 A * 10/1999 Sage et al. ..................... 604/20
5,986,065 A * 11/1999 Wong et al. ............. 530/388.22

OTHER PUBLICATIONS

Birnbaum, Atar, Luo, Hagai, and Siegel, "Ultrasound has synergistic effects in vitro with tirofiban and heparin for thrombus dissolution", Thrombosis Research, 96, (1999) 451–458.*

* cited by examiner

Primary Examiner—Brian L. Casler
Assistant Examiner—Catherine Serke
(74) Attorney, Agent, or Firm—Walter A. Hackler

(57) ABSTRACT

Acute care method and apparatus for treating a patient experiencing thrombotic vascular occlusion includes introducing a selected dose of an active agent proximate a vascular occlusion in the patient in order to lyse the vascular occlusion and radiating the vascular occlusion and active agent.

18 Claims, 1 Drawing Sheet

METHOD AND APPARATUS FOR EMERGENCY TREATMENT OF PATIENTS EXPERIENCING A THROMBOTIC VASCULAR OCCLUSION

The present invention is generally related to method and apparatus for pre-hospital or initial treatment of patients experiencing a thrombotic vascular occlusion, and is more particularly directed to an emergency application of ultrasound and an agent for lysing vascular occlusions or thrombi. Importantly, the agent may not have activity for lysing vascular occlusions without application of ultrasound.

Thrombosis can cause partial or total occlusion of blood vessels which leads to a number of important cardiovascular complications, including unstable angina, acute myocardial infarction (heart attack), cerebral vascular accidents (stroke) pulmonary embolism, deep vein thrombosis and arterial thrombosis.

It is well known that acute myocardial infarction is one of the greatest causes of death in the United States, and it has been recognized that time is of the essence in successfully treating individuals undergoing acute myocardial infarction. Many hospitals and caregiving institutions have established coronary care units with trained personnel and equipment for treating a patient in the shortest time possible upon arrival. However, important time is lost during the delivery of patients to hospitals.

Removal or lysing of vascular occlusions, or clots, may be accomplished through a variety of agents such as, for example, urokinase, streptokinase, aspirin and tissue plasminogen activators, tPA. These clot dissolving agents are generally used in order to lyse clots which have formed in the coronary arteries.

These agents are typically injected into the bloodstream or organ close to the position of the clot. Unfortunately, such agents have a side effect of causing undesirable bleeding in the patient. Thus, patients who may have an ulcer or other bleeding disorder are especially difficult to treat with systemic anticoagulants. Aspirin has found wide use as a clot inhibitor, particularly with respect to clots on the arterial side of circulation. However, aspirin is used as an adjuvant agent to prevent thrombosis and has little if any effect on an established blood clot.

Ultrasound has found use in the dissolution of vascular occlusions. For example, U.S. Pat. Nos. 5,269,291, 5,318,014, 5,362,309, 5,431,662 and 5,474,531, describe intravascular ultrasonic tools for the dissolution of intravascular blockages.

More recently, transcutaneous ultrasound has been found to enhance the activity of thrombolytic agent, for example, see U.S. Pat. Nos. 5,509,896 and 5,695,460. All of the hereinabove referenced patents have been assigned to the assignee of the present application.

Thus, while it has been recognized that the use of ultrasound with an active agent enhances the activity of the agent in lysing of a vascular occlusion, other synergistic properties have not been heretofore discovered. For instance, it has been found in accordance with the present invention that ultrasound shortens the onset of thrombolysis activity of an agent such as, for example, microbubbles or tPA. Accordingly, more rapid onset of dissolution of clots results in less damage from the vascular occlusion because of more rapid opening of the blood vessel and in the restoration of tissue perfusion. In addition, the combination of certain agents and ultrasound could reduce the likelihood of excess bleeding which may significantly increase the likelihood of survival by a patient.

SUMMARY OF THE INVENTION

A method in accordance with the present invention for providing acute care treatment of a patient experiencing thrombotic vascular occlusion generally includes the steps of introducing a selected dose of an agent for acting on a vascular occlusion in the patient in order to lyse the vascular occlusion and irradiating the vascular occlusion and active agent in order to shorten onset and accelerate the effectiveness of lysing action of the agent. In view of the well known urgency of heart attack and stroke matters, i.e., cell death is directly proportional to time, it is of utmost importance to enhance the onset and accelerate the effectiveness of the active agent in lysing the vascular occlusion.

An "active agent" as used herein is meant to include an agent having little or no lysing activity without ultrasound, but exhibiting lysing activity with ultrasound.

The method in accordance with the present invention applies to coronary, cerebral and peripheral vascular (venous or arterial) occlusions and it is found that the active agent may be a thrombolytic agent, anticoagulants, agents which alter blood viscosity and supply nuclei to facilitate microstreaming, cavitation agents that enhance clot disruption (e.g., Hespan, Pentaspan, an intravenous fat emulsion such as intralipid, liposyn, a microbubble medium, and an antiplatelet agent or other suitable lysing agents).

Accordingly, apparatus in accordance with the present invention, includes a self-contained mobile unit for paramedic or emergency treatment of a patient experiencing thrombotic vascular occlusion. In view of the utmost importance of availability, the apparatus includes a plurality of active agents for dissolution of vascular occlusions. A tutored paramedic or physician selects an agent based upon the indication of patient bleeding and intravenously supplies the agent to the vascular occlusion along with transcutaneously radiating the vascular occlusion.

Accordingly, one method in accordance with the present invention includes application of ultrasound transcutaneously. Under certain situations, the ultrasound may be applied intravascularly and the active agent may be introduced proximate the vascular occlusion by direct injection.

BRIEF DESCRIPTION OF THE DRAWINGS

The advantages and features of the present invention will be better understood by the following description when considered in conjunction with the accompanying drawings, in which.

DETAILED DESCRIPTION

Figure 1:
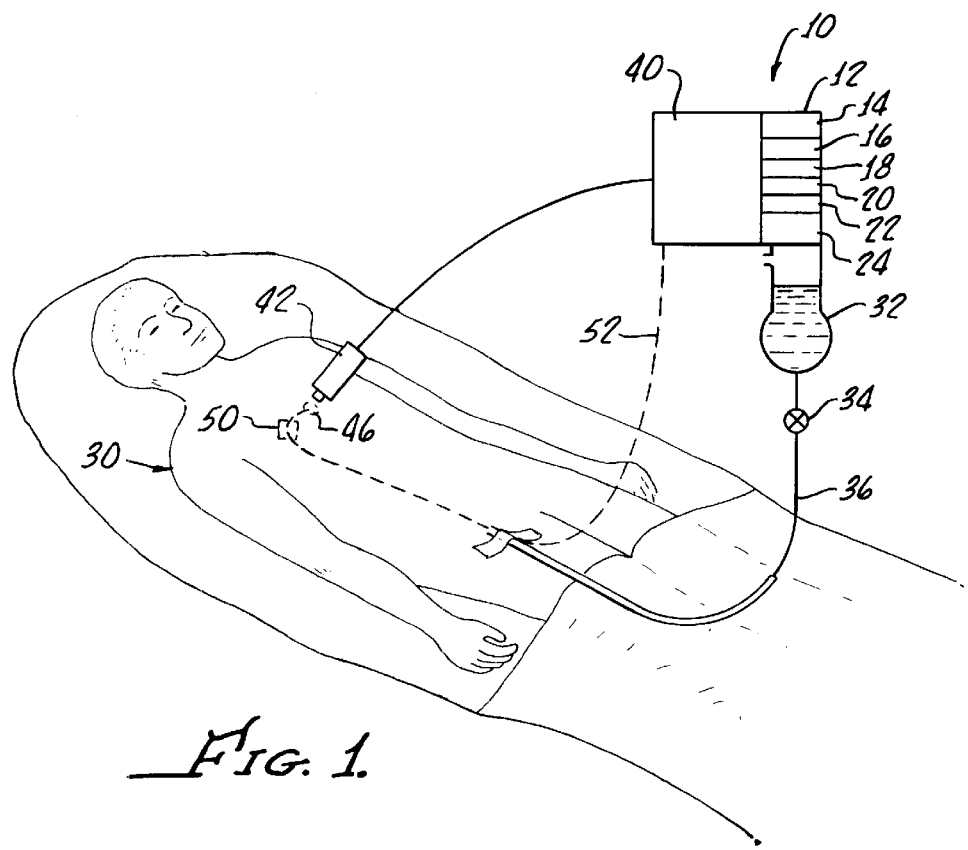
FIG. 1 is a diagram of apparatus in accordance with the present invention which also illustrates the method in accordance with the present invention.

With reference now to FIG. 1, there is shown apparatus 10 for effecting pre-hospital or emergency treatment of a patient experiencing thrombolytic vascular occlusion which includes a self-contained mobile unit 12. As represented by boxes 14, 16, 18, 20, 22, 24, a plurality of active agents for dissolution of vascular occlusion are provided with at least one of the active agents being selected by a paramedic or physician for intravenous introduction into a patient 30 by a vial 32, valve 34 and line 36 which, in combination, provide intravenous means for introducing the selected agent into the patient 30. A vascular occlusion in the present application includes coronary occlusions, cerebral occlusions and peripheral occlusions both venous and arterial. A portable ultrasonic oscillator 40 and transducer 42, in combination, provide a means for transcutaneously radiating a vascular occlusion as indicated by the dotted line at 46. The oscillator 40 may be battery powered, connected to a vehicle electrical system, or connected to a conventional electrical source (not shown) by any conventional means. It should be appreciated that multiple oscillators and transducers (not shown) may be utilized, each having a desirable operating range and properties.

It should be appreciated that ultrasound may be applied intravascularly under proper circumstances, and, in this instance, a miniature transducer, and connected to the oscillator 40 as indicated by the dotted line 50 may be utilized. In this regard, reference is made to U.S. Pat. Nos. 5,269,291, 5,318,014, 2,062,309, 3,431,662, and 4,474,531 which are hereby incorporated in toto by this specific reference thereto as indicating intravascular transducers which may be utilized in accordance with the present invention, all of these patents being assigned to assignee of the present invention.

The transducer 42 may be of any suitable design, for example, as set forth in U.S. Pat. No. 5,879,314 which is incorporated herewith in toto by this reference thereto for the purpose of illustrating the types of transcutaneous transducers which may be suitable for use in accordance with the present invention. The effective frequency range may be from between about 10 kHz to about 2 mHz, with a desirable frequency range being between about 20 kHz and about 500 kHz and another desirable frequency range being between 20 kHz and 50 kHz. The oscillator 40 may be of any suitable type as set forth in any number of the hereinabove referenced U.S. patents.

As hereinabove noted, timing and selection of appropriate lysing agents is of utmost importance.

For example, a criteria for selection between an echo contrast agent such as sonicated albumin, perfluorocarbon, a lysing or thrombolytic agent such as streptokinase or tPA, an anticoagulant such as heparin, antiplatelet agents, such as platelet receptor, like a GP IIb-IIIa inhibitor, such as blockers, Aggrastat, Integrillin, a GP IIb-IIIa platelet inhibitor, Reopro, a hyperalimentation agent such as intravenous fat emulsions, intralipid and liposyn, or another alternative agent such as Hetastarch or other artificial colloidal solutions, such as Pentaspan®, may be as follows.

If there is no indicated bleeding, or significant risk of bleeding, a thrombolitic agent may be selected. If there is possible indicated or risk of bleeding, a GP IIb-IIIa inhibitor may be selected. If there is an absolute contraindication due to risk of bleeding, a microbubble, Hetastarch or Pentaspan is preferably selected.

Other indications may be utilized for agent selection.

It should also be appreciated that a combination of agents may be utilized, for example, an echocontrast agent may be used in combination with a thrombolytic agent. For example, an echocontrast agent may be a perfluorocarbon, such as, for example, the dodecafluropentane colloid dispersion. The echocontrast agent may be a microbubble medium such as free gas bubbles, stabilized gas bubbles, colloidal suspensions, emulsions and aqueous solutions other than dodecafluropentane. A thrombolytic agent may be any agent having suitable activity such as, for example, streptokinase, staphlokinase, urokinase or a tissue plasminogen activator (tPA). These agents are set forth herein only by way of example and it should be appreciated that, as hereinabove recited, any thrombolytic agent has possible use in accordance with the present invention.

As hereinabove noted, a Hetastarch such as HESPAN®, which is a plasma volume expander, has been found to be effective when used in combination with ultrasound for the lysing of vascular occlusions.

Hetastarch is an artificial colloid derived from a waxy starch composed almost entirely of amylopectin. Hydroxyethyl ether groups are introduced into the glucose units of the starch and the resultant material is hydrolyzed to yield a product with a molecular weight suitable for use as a plasma volume expander and erythrocyte sedimenting agent.

As also hereinabove noted, a colloid suspension or pentastarch, such as Pentaspan®. Pentaspan® or Pentastarch is an artificial colloid derived from a waxy starch composed almost entirely of amylopectin. Hydroxyethyl ether groups are introduced into the glucose units of the starch and the resultant material is hydrolyzed to yield a product with a molecular weight suitable for use in an erythrocyte sedimenting agent.

Additionally, the radiation by ultrasound may include continuous or pulse radiation, still more particularly by way of example only, the amount of active agent introduced may be in concentration less than about 2000 microliters.

The combination of ultrasound has the unique effect of accelerating the onset of lysing activity of a GP IIb-IIIa antiplatelet inhibitor such as Reopro or a GP IIb-IIIa blocker such as, for example, Aggrastat and Integrillin.

Figure 2:
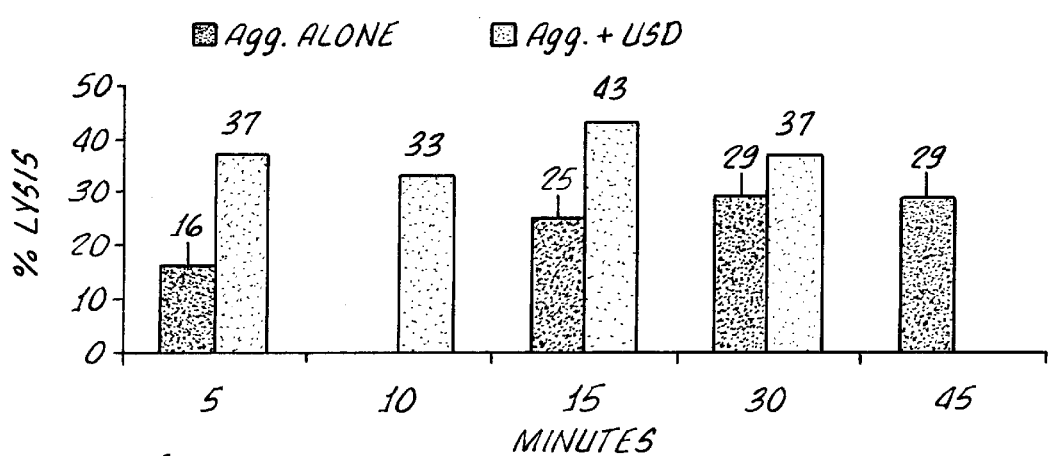
FIG. 2 is a graph of lysing effectiveness with and without ultrasound as a function of time.

FIG. 2 shows a percent of lysing of human blood clots in vitro when blood clots were incubated with Aggrastat alone at the blood concentration achieved in patients being treated with this agent alone at a concentration which is similar to that given therapeutically to patients and in combination with ultrasound at a frequency of 20 kHz applied transcutaneously. It is evident that in five minutes the use of ultrasound more than doubles the lysing activity of the Aggrastat with the overall lysing activity of being less enhanced at, for example, 30 minutes. This onset of lysing activity is important in acute care situations.

Further, the results utilizing ultrasound and tPA and PESDA, a sonicated albumin perfluorocarbon are shown in Tables 1 and 2. The data shown in Tables 1 and 2 on lysing of clots formed by electric induction of thrombotic occlusion of the left anterior descending coronary artery (LAD) to test the effects of PESDA and tPA in combination with transcutaneous ultrasound on reperfusion in a dog model in vivo. As indicated in the Tables, the ultrasound frequencies utilized were 26 kHz and 37 kHz. Heparin was also used in combination and the flow of blood through the arteries indicated as TIMI with a TIMI value of 0 representing no flow and a TIMI value of 3 representing unoccluded flow of blood. Other agents such as antiplatelet agents, such as GP IIb-IIIa inhibitor, microbubble mediums, anti-coagulants volume expanders and agents having a particulate nature such as Hetastarch, Pentaspan, as well as anticoagulants such as Heparin, produce similar results in vitro.

Tables 1 and 2 show data on ultrasound+PESDA and TPA+USD or TPA alone in a dog myocardial infarction model.

The results shown in Tables 1 and 2 indicate that PESDA which has no thrombolytic effect of its own facilitates ultrasound clot lysis in a coronary artery with there being re-establishment of blood flow in 5 of 6 dogs studied after the combination of intravenous PESDA and transcutaneous ultrasound over the dog's chest.

Table 2 shows that in comparison with intravenous tPA, (given in standard doses for humans) the standard thrombolytic drug given to patients with a heart attack, tPA only dissolves the clot in one of four dogs. Even in this case, there was residual clot in the coronary artery. However, when transcutaneous ultrasound over the dog's chest wall, aimed at the heart, is combined with the intravenous tPA, the clots are all dissolved, and there are no significant residual filling defects from blood clots. These data indicate that ultrasound plus a combination of a drug or drugs can be used to more effectively dissolve blood clots in the arteries of the heart to more effectively treat heart attacks.

Also incorporated into the present invention is a method, and corresponding apparatus 10, for treating a patient on a non-acute basis using the ultrasound methods hereinbefore displaced with agents which have no separate lysing activity but exhibit, or are activated, lysing activity when used in combination with ultrasound. As hereinabove noted, such agents include plasma volume expanders

TABLE 1

PESDA plus transcutaneous ultrasound (37 kHz) in a dog model of acute myocardial infarction,
electric induction of a thrombotic occlusion of the left anterior descending coronary artery (LAD)
PESDA treatment (IV bolus: 0.02 ml/kg, IV; 0.18 ml/kg/h)

| | No | | | | | |
|---|---|---|---|---|---|---|
| | 1 | 2 | 3 | 4 | 5 | 6 |
| Date | 6/25/98 | 8/6/98 | 8/7/98 | 8/19/98 | 8/21/98 | 9/9/98 |
| ID | #8-36 | #8-54 | #8-53 | #8-58 | #8-38 | #8-60 |
| Vessel | left ramus | LAD | LAD | LAD | LAD | LAD |
| Method | PESDA + USD | PESDA + USD | PESDA + USD | PESDA + USD | PESDA + USD | PESDA + USD |
| Electricity time | 90 min | 20 min | 80 min | 50 min | 35 min | 20 min |
| Clot age | 60 min | 60 min | 180 min | 120 min | 60 min | 60 min |
| Heparin | no | TIMI 0:1000 IV 1000 IV 1 h later | TIMI 0:1000 IV total 7000 IV | TIMI 0:2000 IV | TIMI 0:1000 IV total 4000 IV | TIMI 0:2000 IV total 12000 IV |
| TIMI during treatment | | | | | | |
| 30 min | TIMI 0 | TIMI 0 | TIMI 0 | TIMI 3 | TIMI 0 | TIMI 0 |
| 60 min | TIMI 2 | TIMI 0 | TIMI 0 | | TIMI 0 | TIMI 0 |
| 90 min | TIMI 2 | TIMI 0 | TIMI 0 | | TIMI 0 | TIMI 0 |
| 120 min | TIMI 3 | TIMI 0 | TIMI 1 | | TIMI 0 | TIMI 1 |
| 150 min | | TIMI 3 | | | TIMI 3 | TIMI 0 |
| 180 min | | | | | | |
| TIMI during observation | | | | | | |
| 30 min | TIMI 3 | TIMI 3 | TIMI 1 | TIMI 3 | TIMI 3 | NA |
| 60 min | TIMI 3 | TIMI 3 | TIMI 1 | TIMI 3 | TIMI 3 | NA |
| Analogram: | patent with filling defects | patent | patent with filling defects | patent with filling defects | patent with minor filling defects | |

TABLE 2

Comparison of reperfusion using t-PA vs t-PA plus transcutaneous ultrasound (26 kHz) in a dog model of acute
myocardial infarction, electric induction of a thrombotic occlusion of the left anterior descending coronary artery (LAD)

| | No | | | | | | |
|---|---|---|---|---|---|---|---|
| | 1 | 2 | 3 | 4 | 5 | 6 | 7 |
| Date | 12/24/98 | 12/31/98 | 1/15/99 | 1/19/99 | 1/21/99 | 1/28/99 | 2/12/99 |
| ID | #8-84 | #8-86 | #8-87 | #8-88 | #8-89 | #8-101 | #8-97 |
| Vessel | LAD | LAD | LAD | LAD | LAD | LAD | LAD |
| Method | t-PA alone | t-PA + USD | t-PA alone | t-PA + USD | t-PA + USD | t-PA alone | t-PA + USD |
| Electricity time | 100 min | 45 min | 200 min | 100 min | 100 min | 70 min | 160 min |
| Clot age | 60 min | 90 min | 120 min | 120 min | 120 min | 120 min | 360 min |
| Heparin | TIMI 0:2000 IV TIMI 3:4000 SC | TIMI 0:1000 IV TIMI 3:2000 SC | TIMI 0:1000 IV | TIMI 0:1000 IV TIMI 3:2000 SC | TIMI 0:1000 IV TIMI 3:1000 SC | TIMI 0:1000 IV TIMI 3:1000 SC | TIMI 0:1000 IV TIMI 1:1000 SC |
| TIMI during treatment | | | | | | | |
| 20 min | TIMI 3 | TIMI 3/15 min | TIMI 0 | TIMI 1 | TIMI 3 | TIMI 3 with residual TH and distal occlusions | TIMI 0 |
| 40 min | N/A | N/A | TIMI 0 | TIMI 1 | TIMI 3 | TIMI 0 | TIMI 1 |
| 60 min | N/A | N/A | TIMI 0 | TIMI 1 | TIMI 3 | TIMI 0 | TIMI 1 |
| 90 min | N/A | N/A | TIMI 0 | TIMI 1 | TIMI 3 | TIMI 0 | TIMI 2 |
| TIMI during observation | | | | | | | |

TABLE 2-continued

Comparison of reperfusion using t-PA vs t-PA plus transcutaneous ultrasound (26 kHz) in a dog model of acute myocardial infarction, electric induction of a thrombotic occlusion of the left anterior descending coronary artery (LAD)

| | No | | | | | | |
|---|---|---|---|---|---|---|---|
| | 1 | 2 | 3 | 4 | 5 | 6 | 7 |
| 30 min | TIMI 3 | TIMI 3 | N/A | TIMI 1 | TIMI 3 | TIMI 0 | TIMI 3 |
| 60 min | TIMI 3 | TIMI 3 | N/A | TIMI 1 | TIMI 3 | TIMI 0 | TIMI 3 |
| 90 min | TIMI 3 | TIMI 3 | N/A | TIMI 3 | TIMI 3 | TIMI 0 | TIMI 3 |
| 90 min angiogram | patent with filling defects | widely patent | LAD occlusion | widely patent | widely patent | LAD occlusion | patent with minor filling defects |
| Serum analysis | | | Yes | Yes | Yes | Yes | Yes | and colloid suspensions such as HESPAN® and PENTASPAN®.

Although there has been hereinabove described a specific arrangement of ultrasonic apparatus and method for thrombi dissolution in accordance with the present invention for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A method for treating a patient experiencing a thrombotic vascular occlusion, the method comprising:
   introducing a selected dose of an agent for acting on a vascular occlusion in the patient in order to lyse said vascular occlusion, said agent being a GP IIb-IIIa platelet blocker selected from a group consisting of Aggrastat and Integrilin; and
   subsequently ultrasonically radiating said vascular occlusion and said active agent in order to shorten onset and enhance effectiveness of lysing action of said active agent.

2. The method according to claim 1 wherein the ultrasound is applied transcutaneously.

3. The method according to claim 1 wherein the ultrasound is applied intravascularly.

4. The method according to claim 2 wherein the active agent is introduced intravenously.

5. The method according to claim 4 wherein the active agent is introduced at an intravascular site of ultrasound application.

6. The method according to claim 1 wherein said vascular occlusion is a coronary occlusion.

7. The method according to claim 1 wherein said vascular occlusion is a cerebral occlusion.

8. The method of claim 1 wherein said vascular occlusion is a peripheral venous or arterial occlusion.

9. The method according to claim 1 wherein the introduction of active agent and ultrasound radiation is performed as an emergency procedure.

10. An acute care method of treating a patient experiencing a thrombotic vascular occlusion, the method comprising:
    selecting an active agent from a group of GP IIb-IIIa platelet blocker consisting of Aggtrastat and Integrilin;
    introducing the selected dose of the active agent into a patient experiencing a thrombotic vascular occlusion in order to lyse said vascular occlusion; and
    subsequently ultrasonically radiating said vascular occlusion in order to shorten agent effectiveness onset of the active agent lysing said vascular occlusion.

11. The method according to claim 10 wherein the ultrasound is applied transcutaneously.

12. The method according to claim 11 wherein the active agent in introduced intravenously.

13. The method according to claim 12 wherein the active agent is introduced at an intravascular site of ultrasound application.

14. The method according to claim 10 wherein the ultrasound is applied intravascularly.

15. The method according to claim 10 wherein said vascular occlusion is a coronary occlusion.

16. The method according to claim 10 wherein said vascular occlusion is a cerebral occlusion.

17. The method according to claim 10 wherein said vascular occlusion is a peripheral venous or arterial occlusion.

18. The method according to claim 10 wherein the introduction of active agents and ultrasound radiation is performed as an emergency procedure.

* * * * *